US00PP35077P2

(12) United States Plant Patent
Kievit et al.

(10) Patent No.: US PP35,077 P2
(45) Date of Patent: Mar. 28, 2023

(54) ***SEDUM* PLANT NAMED 'YELLOW DIAMONDS'**

(50) Latin Name: *Sedum middendorffianum*
Varietal Denomination: Yellow Diamonds

(71) Applicant: Ball Horticultural Company, West Chicago, IL (US)

(72) Inventors: Christa Kievit, Hem (NL); Karl F. Batschke, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/958,585

(22) Filed: Oct. 3, 2022

(51) Int. Cl.
*A01H 5/02* (2018.01)
*A01H 6/32* (2018.01)

(52) U.S. Cl.
USPC ..... Plt./479

(58) Field of Classification Search
USPC ..... Plt./263.1, 479
See application file for complete search history.

(56) References Cited

U.S. PATENT DOCUMENTS

PP32,158 P2 * 9/2020 Hansen ..... A01H 5/02
Plt./479

* cited by examiner

*Primary Examiner* — Karen M Redden
(74) *Attorney, Agent, or Firm* — Audrey Charles

(57) ABSTRACT

A new and distinct cultivar of *Sedum* plant named 'Yellow Diamonds', characterized by its bright yellow-colored flowers, dark green colored foliage, and moderately vigorous, compact-mounded growth habit, is disclosed.

1 Drawing Sheet

Latin name of genus and species of plant claimed: *Sedum middendorffianum.*
Variety denomination: 'Yellow Diamonds'.

BACKGROUND OF THE INVENTION

The present invention relates to a new and distinct cultivar of *Sedum* plant botanically known as *Sedum middendorffianum* and hereinafter referred to by the cultivar name 'Yellow Diamonds'.

The new cultivar originated in a controlled breeding program in Hem, the Netherlands in August 2015. The objective of the breeding program was the development of *Sedum* cultivars having contrasting stem and foliage coloration and a compact-mounded growth habit.

The new *Sedum* cultivar is the result of open-pollination. The female (seed) parent of the new cultivar is the proprietary *Sedum middendorffianum* breeding selection coded C625-4, not patented, characterized by its medium yellow-colored flowers, medium grey-green colored foliage, and moderately vigorous, compact-mounded growth habit. The male (pollen) parent of the new cultivar is unknown. The new cultivar was selected as a single flowering plant within the progeny of the above stated open-pollination during July 2016 in a controlled environment in Hem, the Netherlands.

Asexual reproduction of the new cultivar by terminal stem cuttings since July 2016 in Hem, the Netherlands and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Yellow Diamonds' as a new and distinct cultivar of *Sedum* plant:

1. Bright yellow-colored flowers;
2. Dark green colored foliage; and
3. Moderately vigorous, compact-mounded growth habit.

Plants of the new cultivar differ from plants of the female parent primarily in having brighter yellow-colored flowers and darker green-colored foliage.

Of the many commercially available *Sedum* cultivars, the most similar in comparison to the new cultivar is 'Little Miss Sunshine', U.S. Plant Pat. No. 30,039. However, in side-by-side comparison, plants of the new cultivar differ from plants of 'Little Miss Sunshine' in at least the following characteristics:

1. Plants of the new cultivar have mature stems colored with a dark red overlay unlike the green stems of plants of 'Little Miss Sunshine'; and
2. Plants of the new cultivar smaller diameter flowers than plants of 'Little Miss Sunshine'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Yellow Diamonds'. The plants were approximately four months old and grown three plants per pot in one-gallon containers for approximately two months in an outdoor nursery environment in West Chicago, Ill. Plants were given one pinch at approximately two weeks before transplant and another one week after transplant.

DETAILED BOTANICAL DESCRIPTION

Figure 1:
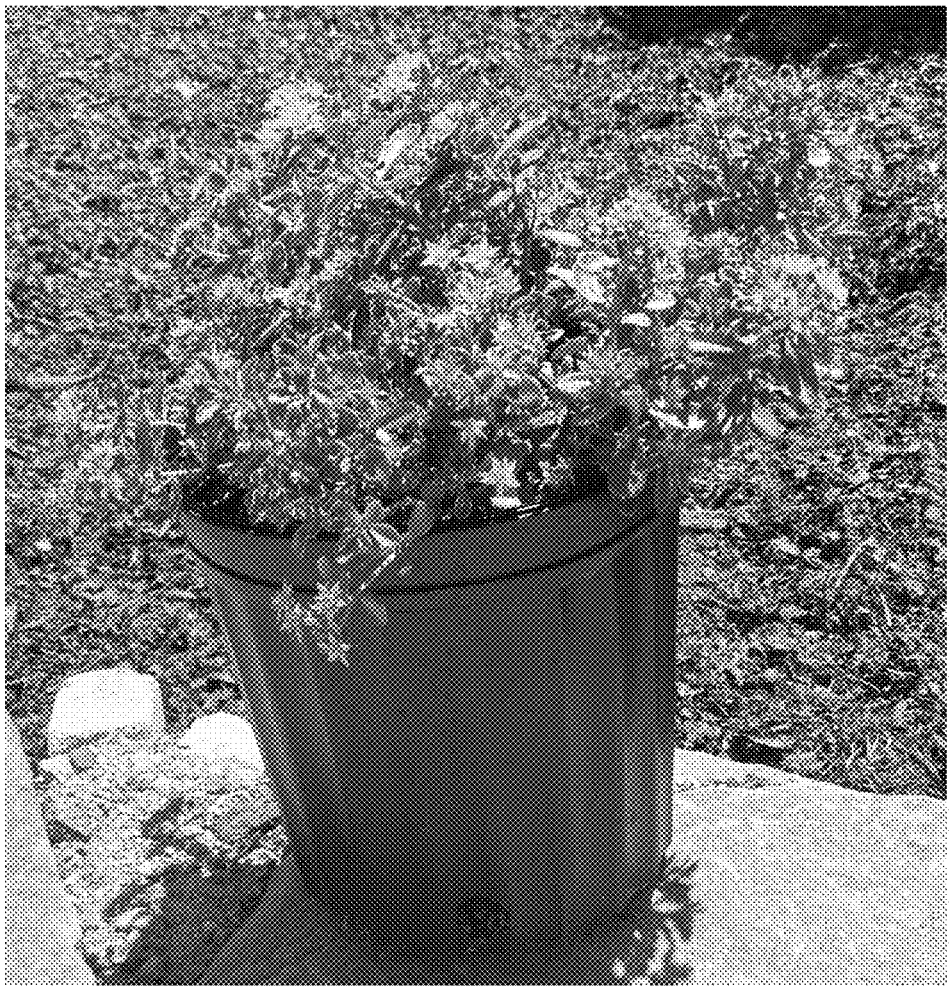
FIG. 1 illustrates a side view of the overall growth and flowering habit of 'Yellow Diamonds'.
Figure 2:
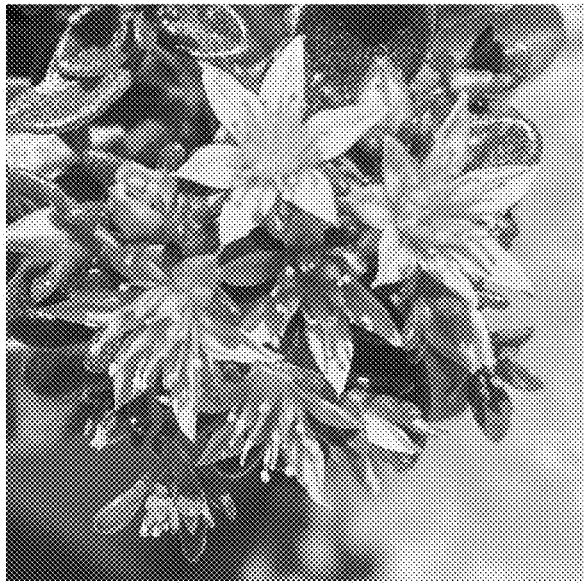
FIG. 2 illustrates a close-up view of an inflorescence of 'Yellow Diamonds'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in June 2022 under natural light conditions in Naperville, Ill.

The following descriptions and measurements describe approximately four-month old plants produced from cuttings from stock plants and grown in a polycarbonate-covered greenhouse under conditions comparable to those used in commercial practice. Approximately six weeks after sticking, rooted plants were transplanted three plants per one-gallon containers utilizing a soilless growth medium and grown for three weeks. Plants were then transferred to an outdoor nursery environment in West Chicago, Ill. and grown for approximately two months. Plants were given one pinch at approximately two weeks before transplant and another one week after transplant. Prior to transplant plants were grown in liners in a polycarbonate greenhouse in West Chicago, Ill. Greenhouse temperatures were maintained at approximately 70° F. to 75° F. (21.1° C. to 23.9° C.) during the day and approximately 60° F. to 65° F. (15.6° C. to 18.3° C.) during the night. Supplemental lighting was used. Measurements and numerical values represent averages of typical plants.

Botanical classification: *Sedum middendorffianum* 'Yellow Diamonds'.

Parentage:

*Female parent*.—Proprietary *Sedum middendorffianum* breeding selection coded C625-4, not patented.

*Male parent*.—Unknown.

Propagation:

*Type cutting*.—Terminal stem.

*Time to initiate roots*.—Approximately 2 weeks.

*Time to produce a rooted cutting*.—Approximately 5 to 6 weeks.

*Root description*.—Fine to medium, fibrous.

*Rooting habit*.—Freely branching.

Plant description:

*Commercial crop time*.—Approximately 8 to 10 weeks from a rooted cutting to finish in a 15 cm pot.

*Growth habit and general appearance*.—Herbaceous perennial; succulent; moderately vigorous, compact-mounded growth habit.

*Hardiness*.—USDA Zone 5a (−20° F. to −15° F./−28.9° C. to −26° C.).

*Size*.—Height from soil level to top of plant plane: Approximately 17.0 cm. Width: Approximately 25.0 cm.

*Branching habit*.—Freely branching. Quantity of branches per plant: Approximately 4 main basal branches with approximately 14 laterals per main branch.

*Lateral branch*.—Shape: Round in cross section. Strength: Strong, flexible. Length to base of peduncle: Approximately 11.0 cm. Diameter: Approximately 2.0 mm to 3.0 mm. Length of central internode: Approximately 1.0 cm. Texture: Moderately pubescent. Color of young stem: 146D. Color of mature stem: 146D with a moderate to heavy overlay of 187A.

Foliage description:

*General description*.—Quantity of leaves per lateral branch: Approximately 11. Fragrance: Not detected. Form: Simple. Arrangement: Dextrorse.

*Leaves*.—Aspect: Acute angle to perpendicular to stem. Shape: Obovate to oblanceolate, thick fleshy. Margin: Entire with broadly serrate on distal half to third. Apex: Rounded. Base: Attenuate, sessile. Venation pattern: Pinnate. Length of mature leaf: Approximately 2.7 cm. Width of mature leaf: Approximately 1.1 cm. Thickness: Approximately 1.5 mm. Texture of upper and lower surfaces: Glabrous. Color of upper surface of young and mature foliage: Closest to 137A with indistinguishable venation. Color of lower surface of young and mature foliage: Closest to 146B with indistinguishable venation.

Flowering description:

*Flowering habit*.—'Yellow Diamonds' is a long-day obligate, freely flowering blooming from late spring through summer under outdoor growing conditions.

*Lastingness of individual flower*.—Approximately 4 to 6 days, persistent.

Inflorescence description:

*General description*.—Type: Axillary and terminal compound cyme. Quantity of open inflorescences per plant: Approximately 10. Fragrance: Not detected. Length or height of inflorescence: Approximately 3.5 cm. Width of inflorescence: Approximately 4.5 cm. Quantity of fully-open flowers per inflorescence: Approximately 4 to 9.

*Peduncle*.—Strength: Strong, flexible. Aspect: Erect. Length: Approximately 1.5 cm to 2.5 cm. Diameter: Approximately 2.0 mm. Texture: Moderately pubescent. Color: 146D with a moderate to heavy overlay of 187A.

Flower description:

*Type*.—Single, actinomorphic.

*Bud just before opening*.—Shape: Ovoid. Length: Approximately 6.0 mm. Diameter: Approximately 3.0 mm. Texture: Glabrous. Color: 1A with 146D.

*Corolla*.—Shape: Primarily rotate, slightly cupped. Aspect: Facing upward and outward. Diameter: Approximately 1.2 cm. Depth: Approximately 5.0 mm.

*Petals*.—Quantity per flower: 5 to 6. Shape: Elliptic. Margin: Entire. Apex: Acute. Base: Attenuate. Length: Approximately 6.0 mm. Width: Approximately 2.0 mm. Texture of upper and lower surfaces: Glabrous. Color of upper surface when first and fully open: 2B. Color of lower surface when first and fully open: 1C with midvein of 146D.

*Calyx*.—Shape: Primarily rotate, slightly cupped. Diameter: Approximately 9.0 mm.

*Sepals*.—Quantity per flower: 5 to 6. Shape: Elliptic, fleshy. Margin: Entire. Apex: Acute. Base: Truncate. Length: Approximately 5.0 mm. Width: Approximately 2.0 mm. Texture of upper and lower surfaces: Glabrous. Color of inner and outer surfaces: 137A with base of 146D.

*Pedicel*.—Strength: Strong, flexible. Aspect: At an acute angle to stem. Length: Approximately 5.0 mm to 1.0 cm. Diameter: Approximately 1.0 mm. Texture: Glabrous. Color: 146D sometimes with faint overlay of 187A.

*Reproductive organs*.—Androecium: Stamen quantity: 10 to 12 per flower. Stamen length: Approximately 4.0 mm. Filament color: N144A. Anther shape: Ellipsoid, basifixed. Anther length: Less than 1.0 mm. Anther color: 16B. Pollen amount: Sparse. Pollen color: 16D. Gynoecium: Pistil quantity: 5 to 6 per flower. Gynoecium shape: Ovoid. Gynoecium length: 4.0 mm. Gynoecium width at widest point: Approximately 2.0 mm. Gynoecium color: N144A.

Seed and fruit production: Neither seed nor fruit production has been observed.

Disease and pest resistance: Resistance to pathogens and pests common to *Sedum* has not been observed.

What is claimed is:

1. A new and distinct cultivar of *Sedum* plant named 'Yellow Diamonds', substantially as herein illustrated and described.

* * * * *